(12) United States Patent
Mueth et al.

(10) Patent No.: US 7,574,076 B2
(45) Date of Patent: Aug. 11, 2009

(54) APPARATUS FOR OPTICALLY-BASED SORTING WITHIN LIQUID CORE WAVEGUIDES

(75) Inventors: Daniel Mueth, Chicago, IL (US); Evan Tanner, Chicago, IL (US); Joseph Plewa, Park Ridge, IL (US); Osman Akcakir, Chicago, IL (US)

(73) Assignee: Arryx, Inc., Chicago, IL (US)

( * ) Notice: Subject to any disclaimer, the term of this patent is extended or adjusted under 35 U.S.C. 154(b) by 8 days.

(21) Appl. No.: 11/399,569

(22) Filed: Apr. 7, 2006

(65) Prior Publication Data

US 2006/0257089 A1 Nov. 16, 2006

Related U.S. Application Data

(60) Provisional application No. 60/669,357, filed on Apr. 8, 2005.

(51) Int. Cl.
*G02B 6/12* (2006.01)
*G02B 6/032* (2006.01)
*G02B 6/10* (2006.01)

(52) U.S. Cl. .................... 385/14; 385/125; 385/132

(58) Field of Classification Search .............. 385/125, 385/132, 14
See application file for complete search history.

(56) References Cited

U.S. PATENT DOCUMENTS 6,983,093 B2 * 1/2006 Fraval et al. ............. 385/125
7,068,874 B2 * 6/2006 Wang et al. ............... 385/16
7,176,445 B2 * 2/2007 Curtis et al. ............. 250/221
2005/0207940 A1 * 9/2005 Butler et al. ............... 422/73

OTHER PUBLICATIONS

MacDonald, M.P., Spalding, K. Dholakia, "Microfluidic sorting in an optical lattice", Nature, vol. 426, 421-4 (2003).*
Ke, P.C., M. Gu, "Characterization of trapping force on metallic Mie particles", Applied Optics, vol. 38, No. 1, 106-7 (1999).*
F. Dubois, PH. Emplit, and O. Hugon, "Selective mode excitation in graded-index multimode fiber by a . . .", Optics Letters, Apr. 1, 1994, 433-435, vol. 19 No. 7.
D. McGloin and K. Dholakia, "Bassel beams: diffraction in a new light", Contemporary Physics, Jan.-Feb. 2005, 15-28, vol. 46, No. 1.

* cited by examiner

*Primary Examiner*—Charlie Peng
(74) *Attorney, Agent, or Firm*—Jean C. Edwards, Esq.; Akerman Senterfitt

(57) ABSTRACT

The present invention is related to an apparatus for the sorting of particles in a fluid medium flowing within a liquid-core waveguide, by combining customized light intensity patterns formed inside the waveguide, and diluting the suspension of particles (i.e., cells, blood, nanoparticles, etc.) flowing within the fluid medium of the waveguide. With this customized light intensity pattern, which controls the optical forces introduced by the light confined within the waveguide, and the control of the hydrodynamic forces introduced by the liquid flow (or multiple channel liquid flows), the sorting of particles can be achieved.

101 Claims, 10 Drawing Sheets

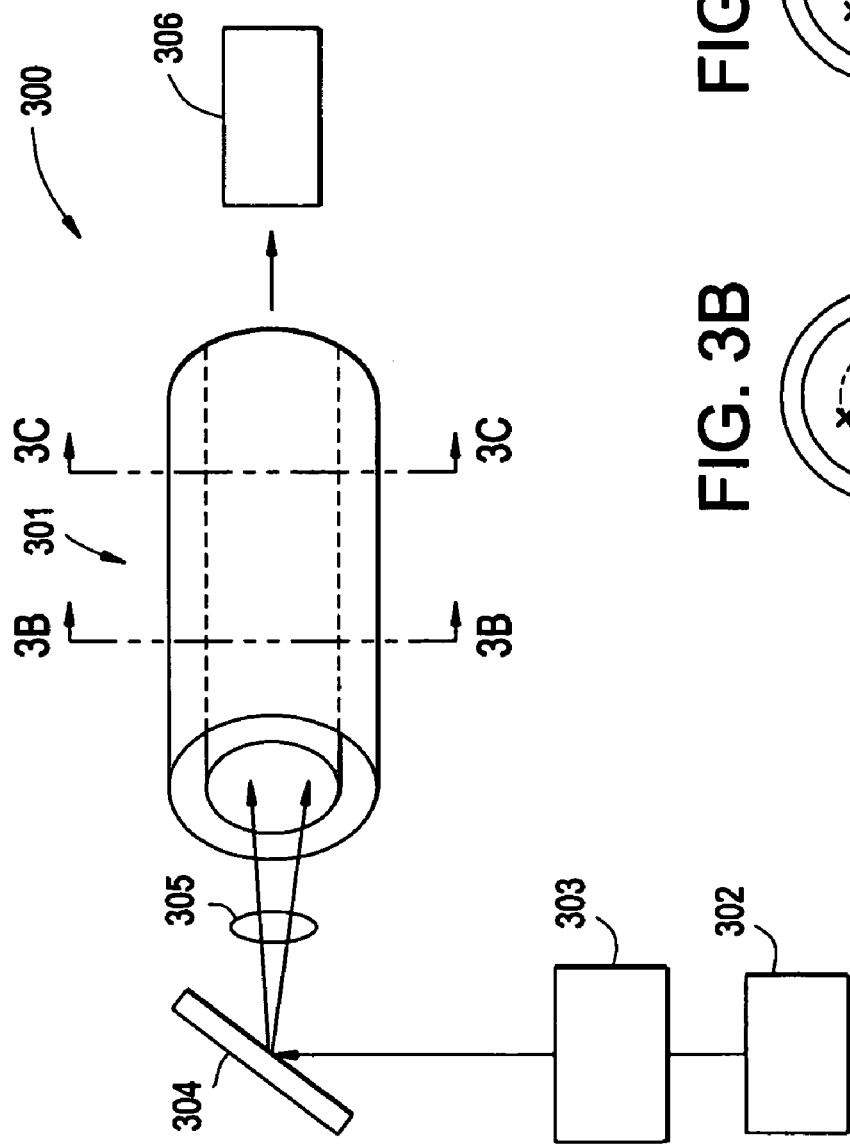
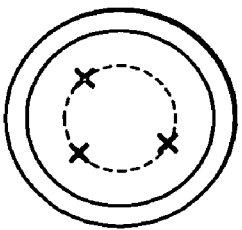
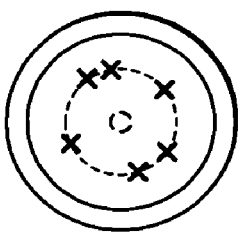

US 7,574,076 B2

APPARATUS FOR OPTICALLY-BASED SORTING WITHIN LIQUID CORE WAVEGUIDES

CROSS-REFERENCE TO RELATED APPLICATIONS

The present application claims priority from U.S. Provisional Patent Application No. 60/669,357, filed Apr. 8, 2005, the entire contents of which are herein incorporated by reference in their entirety.

BACKGROUND OF THE INVENTION

1. Field of the Invention

The present invention is related to an apparatus for the sorting of particles in a fluid medium flowing within a liquid-core waveguide, by combining customized light intensity patterns formed inside the waveguide, and diluting the suspension of particles (i.e., cells, blood, nanoparticles, etc.) flowing within the fluid medium of the waveguide. With this customized light intensity pattern, which controls the optical forces introduced by the light confined within the waveguide, and the control of the hydrodynamic forces introduced by the liquid flow (or multiple channel liquid flows), the sorting of particles can be achieved.

2. Description of the Related Art

Liquid-core optical waveguides (also known as light-guides) have been used to couple fluorescently or luminescently generated light in a liquid sample located in the liquid core as light detectors for diagnostic purposes.

Although eigenmodes have been successfully launched into multi-mode optical fibers (see F. Dubois, Ph. Emplit, and O. Hugon, Optics Letters, Vol. 19 No. 7, Apr. 1, 1994) via a spatial light modulator (SLM), the optical fibers used have solid cores, and so are only useful as conduits for light. Further, although optical fibers with solid cores have been used with diffractive optical elements for launching in specific eigenmodes, the purpose has been only to study their propagation characteristics.

However, in none of the above experiments, has there been any indication that liquid-core waveguides could be used to sort particles/cells.

BRIEF DESCRIPTION OF THE DRAWINGS

FIG. 3A is a perspective schematic diagram showing yet another embodiment using a spatial light modulator to introduce multiple eigenmodes or time varying series of eigenmodes in a liquid core waveguide apparatus for sorting particles, consistent with the present invention.

FIG. 3B is a cross-section along line B of the liquid core waveguide of FIG. 3A.

FIG. 3C is a cross-section along line C of the liquid core waveguide of FIG. 3A.

SUMMARY OF THE INVENTION

Figure 1:
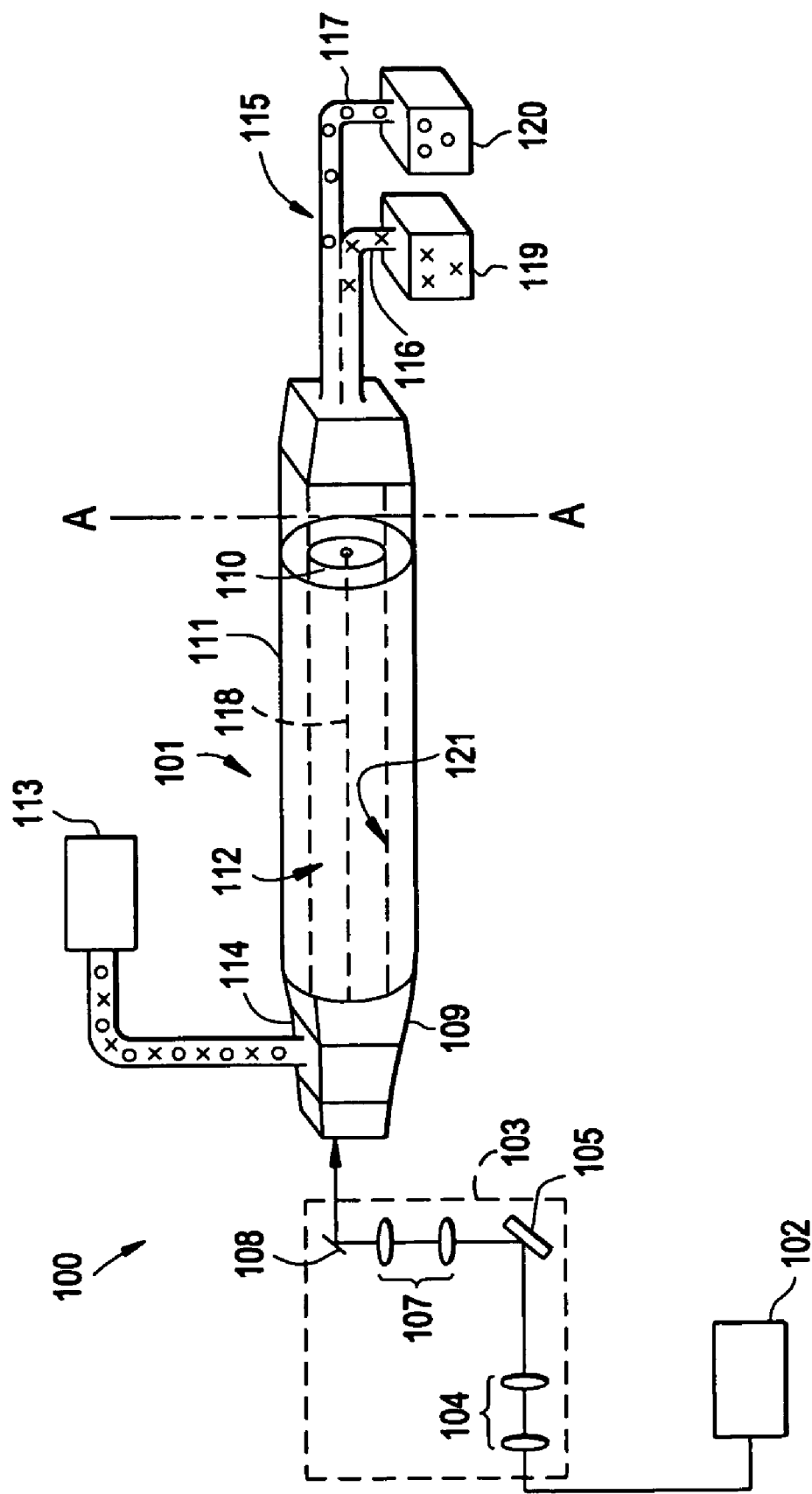
FIG. 1 is a schematic diagram showing a liquid core waveguide apparatus for sorting particles according to one embodiment consistent with the present invention.

The present invention is related to an apparatus for the sorting of particles in a fluid medium flowing within a liquid-core waveguide, by combining customized light intensity patterns formed inside the waveguide, and diluting the suspension of particles (i.e., cells, blood, nanoparticles, etc.) flowing within the fluid medium of the waveguide. With this customized light intensity pattern, which controls the optical forces introduced by the light confined within the waveguide, and the control of the hydrodynamic forces introduced by the liquid flow (or multiple channel liquid flows), the sorting of particles can be achieved.

In the present invention, it is noted that photons in a light field carry momentum, which may be transferred to surfaces by refractive index mismatches. Therefore, microscopic particles/cells, which have indices of refraction greater than the surrounding medium may be trapped by light that is brought to a tight focus with a high numerical aperture microscope objective. This focal spot acts as an optical trap. There are two types of forces which act on particles in optical traps. Scattering forces which push particles down the beam (photon momentum transfer to the particle) and gradient forces which are a function of the gradient of light intensity across the particle and which cause particles to be attracted to the trap center where the net gradient forces are zero. High numerical aperture objectives allow high gradient forces to be applied, counteracting the competing tendency of the scattering forces to push the particles down the beam without trapping them. The trapping force on a particle is a function of the light intensity distribution, polarization, wavelength, refractive index of particle, refraction index of liquid medium surrounding particle, shape of particle. Thus, particles that have differing indices of refraction and/or shapes will feel differing amounts of optical forces.

The present invention has utilized this principle to sort different particles based on the different optical forces exerted on them. For example, in the presence of fluid flow, an optically trapped particle will feel an additional hydrodynamic drag force, which may be sufficient to dislodge one type of particle but not another, when trapped in identical optical traps.

In the optical trapping geometry described above, light that converges towards the focus forming the optical trap then diverges away, and is not useful for forming another trapping pattern. The present invention includes devices that are capable of applying optical forces on particles through an extended structure that is designed in a way to maintain light intensity patterns along its length. Such an extended structure or flow tube will be filled with a liquid that has a dilute concentration of particles. Light that is launched into the flow tube will stay confined within the flow tube by the inner reflective surfaces or by a material that permits total internal reflection of the light within the flow tube (i.e. definition of a liquid-core optical waveguide). Since the cross-sectional dimensions of the flow tube are typically significantly larger than the wavelength of light, optically the flow tube supports multiple eigenmodes or patterns of light that have a constant profile along the length of the tube (i.e. flow tube acts as a liquid-core optical waveguide).

For example in a flow tube with cylindrical geometry, the eigenmodes defined by Bessel functions may be supported. The present invention allows an arbitrary light pattern, including arbitrary eigenmodes, to be launched into the flow tube (liquid-core optical waveguide). The benefit of having a eigenmode launched into the flow tube is that the cross-sectional pattern of light is maintained along the length of the tube, allowing the light to be reused so that it is able to exert optical forces on many particles along the length of the tube.

In the present invention, a computer controlled spatial light modulator(s) or static diffractive optical element(s) is used to apply phase delays across segments of the wavefront of a laser source to generate the desired patterns of light in the liquid core waveguide (i.e., eigenmodes, Bessel beams, etc.).

In one embodiment consistent with the present invention, an apparatus for sorting particles/cells includes a liquid core waveguide into which light is directed from a light source, such as a laser, which outputs light directed via coupling optics. The coupling optics includes a computer controlled diffractive optical element (DOE) such as a spatial light modulator (SLM), which directs a "custom light intensity pattern" into the liquid core waveguide. The liquid core waveguide includes an external portion, and a central hollow portion with an inner surface. A dilute suspension of particles/cells is inputted through a liquid input area, and into the hollow portion of the waveguide. After traveling the entire length of the waveguide and being subjected to the custom light intensity patterns generated, the solution flowing through the hollow portion, flows out into a collection area where the solution is separated into constituent parts. A coating may be disposed on the inner surface of the hollow portion, and can be made of a reflective material that enables internal total reflection, to create the functioning waveguide which can support the "custom light intensity pattern" or eigenmodes launched into the waveguide.

In an alternative embodiment, the waveguide's external portion can be made of a material with an index of refraction lower than the solution flowing through the hollow portion, which would achieve the same result.

Another embodiment consistent with the present invention includes a doughnut-shaped eigenmode (i.e., a Bessel function) in a cylindrically shaped waveguide. If the eigenmode is a Bessel function, the light input would be Bessel beams, When a solution with particles/cells for sorting, is input from a reservoir, particles that have a higher refractive index will be preferentially attracted to the tube of light or doughnut region, while the particles with relatively lower indices of refraction will stay in the central region. The particles may be collected via an annular-shaped collection output, downstream of the waveguide, in different collection fractions.

In another embodiment consistent with the present invention, an apparatus for sorting particles/cells, including a liquid core waveguide, into which light is introduced from a light source via coupling optics, a spatial light modulator (SLM) introduces multiple eigenmodes or a time varying series of eigenmodes into the liquid core waveguide, which creates a controlled time dependent variation in the cross-sectional intensity profile for use in sorting.

In another embodiment of an apparatus for sorting particles/cells, including a liquid core waveguide, into which light is introduced, eigenmodes can selectively be launched into the fiber, and hydrodynamic forces controlled by the fluid input, through which the solution containing the particles/cells to be sorted is introduced, and gravitational forces, are combined with optical forces within the waveguide, to selectively direct the desired particles into an outlet collection area, for sorting.

In an alternative embodiment, electric or magnetic fields applied using electrodes, for example, used in combination with optical forces within the waveguide, assist in sorting particles into different output channels.

In yet another alternative embodiment, light from a light source and coupling optics, including a spatial light modulator, is directed into the waveguide, and integrated into a centrifuge with the liquid-core waveguide containing a density gradient chamber for the purposes of sorting on the basis of optical characteristics as well as density. A device that fits into a centrifuge would provide an additional physical parameter to separate the nanoparticle fractions in solution (i.e., fractionation as a result of differential responses to light fields in combination with density).

In yet another embodiment consistent with the present invention, one specific eigenmode or "custom light intensity pattern" for sorting uses Bessel beams introduced into the liquid core waveguide (which would be an example of one type of eigenmode). Objects (i.e., particles, cells, nanoparticles, etc.) flowing within the liquid core waveguide medium exposed to the Bessel beam intensity pattern or line of high intensity light can be trapped by optical forces and be confined along the line defined by the optical axis.

While it has been shown that Bessel beams may reform after being partially obstructed along the optical axis, an alternative method of regeneration of the beam as disclosed by the present invention, is to launch it within a reflective/totally internally reflective hollow-core cylinder (liquid core waveguide).

In one example of this embodiment consistent with the present invention, an apparatus includes a repeating Bessel beam embodiment, which includes a laser, axicon, and cylinder with a highly reflective, sub-wavelength roughness interior. The reflective inner surface of the cylinder or waveguide allows the rays, after they have converged to make the Bessel beam, to be reflected back towards the optical axis so that another Bessel beam may be reformed.

In one exemplary embodiment of an apparatus for sorting particles/cells, consistent with the present invention, light can be confined within a liquid-core waveguide or a resonant cavity. In the embodiment using a waveguide, the waveguide is incorporated in a flow chip which can be used to direct the solution around the waveguide, passing through the nanoporous input holes on the sides of the waveguide. Nanoparticles suspended within the fluid interact with the custom light pattern inside the waveguide and have their position deflected so that when the flow carries the particles out of the waveguide on the other side, the nanoparticles can be easily sorted into different output channels.

In an alternative embodiment, the resonant cavity is incorporated with the flow chip, and typically has one partially reflective end mirror through which light is initially launched into the system from a laser, and the other end mirror which can be totally reflective.

In another embodiment consistent with the present invention, an apparatus for sorting particles/cells, would include a structure where the whole stream of solution can be introduced into the liquid-core waveguide through the ends using nanoporous membranes, allowing all of the solution to interact with the light fields inside the liquid core waveguide.

In yet another embodiment consistent with the present invention, an apparatus for sorting particles/cells involves using a liquid core waveguide which is also a resonant cavity, is coupled with a nanoparticle flow channel allowing the whole flow to interact with the light field inside the waveguide.

In yet another embodiment consistent with the present invention, liquid core waveguides may have non-cylindrical symmetry (i.e., rectangular, for example).

In yet another embodiment consistent with the present invention, only a portion of the flow is introduced or exposed to light from the liquid core waveguide through a sub-wavelength opening.

In other embodiments consistent with the present invention, and as discussed above, the light field may also be an evolving set of eigenmodes which may be introduced with a computer controlled spatial light modulator, allowing sorting based on differential optical entrainment. At the end of the chamber/cavity, based on the final equilibrium positions in the flow stream, the flow may be sorted into separate fractions.

Finally, in other embodiments consistent with the present invention, and as described above, the liquid solution flowed into the waveguide may be purified by sorting out particles which interact with the light and collecting the remaining solution instead of the particles.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to an apparatus including waveguides and optical forces operating therein, and introduces the novel idea of inputting custom light intensity patterns into liquid core waveguides for sorting of particles, as well as specifics on how to introduce such eigenmodes. One application, among several, of the present invention, is blood sorting.

Light exerts relatively small radiation pressure forces on suspended particles or cells (due mainly to the small index mismatch between the cells and plasma). "Light" is typically referred to as visible light but light can include all parts of the electromagnetic spectrum with wavelengths ranging from ultraviolet (UV) 200 nm to Near Infrared (2,500 nm). In a disperse suspension of particles or cells, the differential action of radiation pressure on different components in the solution may be used as the basis for particle/cell sorting.

In order to achieve significant displacement of cell/particle fractions for fractionation purposes at high-throughput, the interaction time of the light with the flowing particles/cells must be high. One embodiment of the present invention describes a device 100 that allows high light intensities and long interaction times by confining both the light and the particle/cell flow in the same geometry, called a liquid core waveguide 101.

FIG. 1 is a schematic diagram showing one embodiment of an apparatus 100 for sorting particles/cells, which includes a liquid core waveguide 101. The apparatus 101 includes a light source 102, such as a laser, which outputs light that is directed via coupling optics 103 into the liquid core waveguide 101.

The coupling optics 103 includes lenses 104, which directs the light onto a computer controlled diffractive optical element (DOE) 105, such as a spatial light modulator (SLM). The diffracted beam is translated through lenses 107, incident onto a gimbal mounted mirror 108, and inputted into the liquid core waveguide 101 through a light input window 109.

Thus, a computer generated hologram is generated by laser 102 which shines a beam through the computer controlled spatial light modulator 105, and through lens 104, 107, for example. The lenses act as a beam reducer so that the beam efficiently couples into the opening of the liquid-core waveguide 101. Thus, a "custom light intensity pattern" is generated to be launched into the liquid core waveguide 101.

Note that the coupling optics 103, can be arranged in various configurations in order to improve efficiency and effectiveness, as long as the desired custom light intensity pattern is achieved.

The liquid core waveguide 101 includes an external portion 111, and a central hollow portion 110 with an inner surface 112, with a central optical axis 118 running down a center of the waveguide 101. A pumping mechanism 113 introduces a dilute suspension of particles/cells, or whatever is desired to be sorted, through a liquid input area 114, and into the hollow portion 110 of the waveguide 101.

The central hollow portion 110 has an internal dimension that is larger than the particles to be sorted, which enables the flow of the particles through it, and allows the custom light pattern generated by the coupling optics 103 to act on the particles and direct them into different target regions within the central liquid core of the waveguide 101.

After traveling the entire length of the waveguide 101 and being subjected to the custom light intensity patterns generated, the solution flowing through the hollow portion 110, flows out into a collection area 115 while the light exits the waveguide 101. The collection area 115 (see along line A in FIG. 1) has output channels 116, 117 configured in a space relative to the hollow portion 110, and the particles/cells which exit the waveguide 101 separated into constituent parts via channels 116, 117, are collected into sorted particles or fractions 119, 120.

To have a functioning waveguide 101 to sort particles, total internal reflection of light at the inner surface 112 of the liquid-filled core or hollow portion 110, is necessary. Therefore, a coating 121 may be disposed on the inner surface 112 of the follow portion 110, the material of the coating 121 whose index of refraction (at the wavelength of the laser) is less than that of the solution flowing through the core 101. In other words, the coating 121 could be made of a material that enables internal total reflection, to create the functioning waveguide 101 which can support the "custom light intensity pattern" or eigenmodes launched into the waveguide 101 without substantial losses of light, and which can act on the particles to be sorted along the entire length of the waveguide 101.

For suspensions in water (i.e., with an index of refraction 1.33), for example, a coating material such as Teflon AF®, for example, which has an index of refraction 1.29-1.31, may be used to coat the insides of the hollow portion 110 and generate a liquid-core waveguide 101. However, one of ordinary skill in the art would know that the inner surfaces of the liquid-core waveguide 101 may be coated with a reflective material, or any material that enables total internal reflection at the wavelengths used, for the solution flowed in (i.e., such that the refractive index of inner coating $n_{ic}(\lambda)$ at wavelength $\lambda$, is less than the refractive index of the solution, $n_{solution}(\lambda)$ or, $n_{ic}(\lambda) < n_{solution}(\lambda)$).

In an alternative embodiment, the waveguide's external portion 111 can be made of a material with an index of refraction lower than the solution flowing through the hollow portion 110, which would achieve the same result.

The device 100 shown in FIG. 1, can be used for various applications. For the purposes of sorting using light, the light must act differentially on each of the components. For example, in the case of blood sorting, the index mismatch of platelets is significantly less than that of red blood cells, allowing the red blood cells to be pushed more easily by the laser light (i.e., the Q factor ("Q" is the proportionality constant between the light intensity and force on the cell due to the light's momentum transfer to the cell), for red blood cells is calculated to be ~5× larger than for platelets, for plane wave incidence).

Thus, a central spot blocker for the k=0 component at the common focal plane, blocks out the $0^{th}$ order beam off the surface of the spatial light modulator 105. Accordingly, the cells with a higher Q factor (i.e., red blood cells) can be guided by the evolving mode profile while the lower Q factor cells (e.g., platelets) will be significantly less optically entrained, allowing the cells to be fractionated depending on their cross-sectional position. Thus, particle/cell solution output is split up into different fractions 119, 120 based on differential optical entrainment—achieving sorting.

For the sorting of particles like red blood cells, which are on the order of 10 microns, the internal diameter of the waveguide or flow tubing 101 (for example, a hollow multi-mode optical fiber) must be much larger than the wavelength of light in order to efficiently flow solutions of blood cells through it. Such large dimensions mean that multiple optical modes can be supported, although the flat cross-sectional intensity profile of standard multi-mode propagation is of no use for the purposes of sorting. However in the present invention, using custom light patterns inside the waveguide (as opposed to the standard intensity profile mentioned above), sorting of particles/cells can be achieved.

Figure 2:
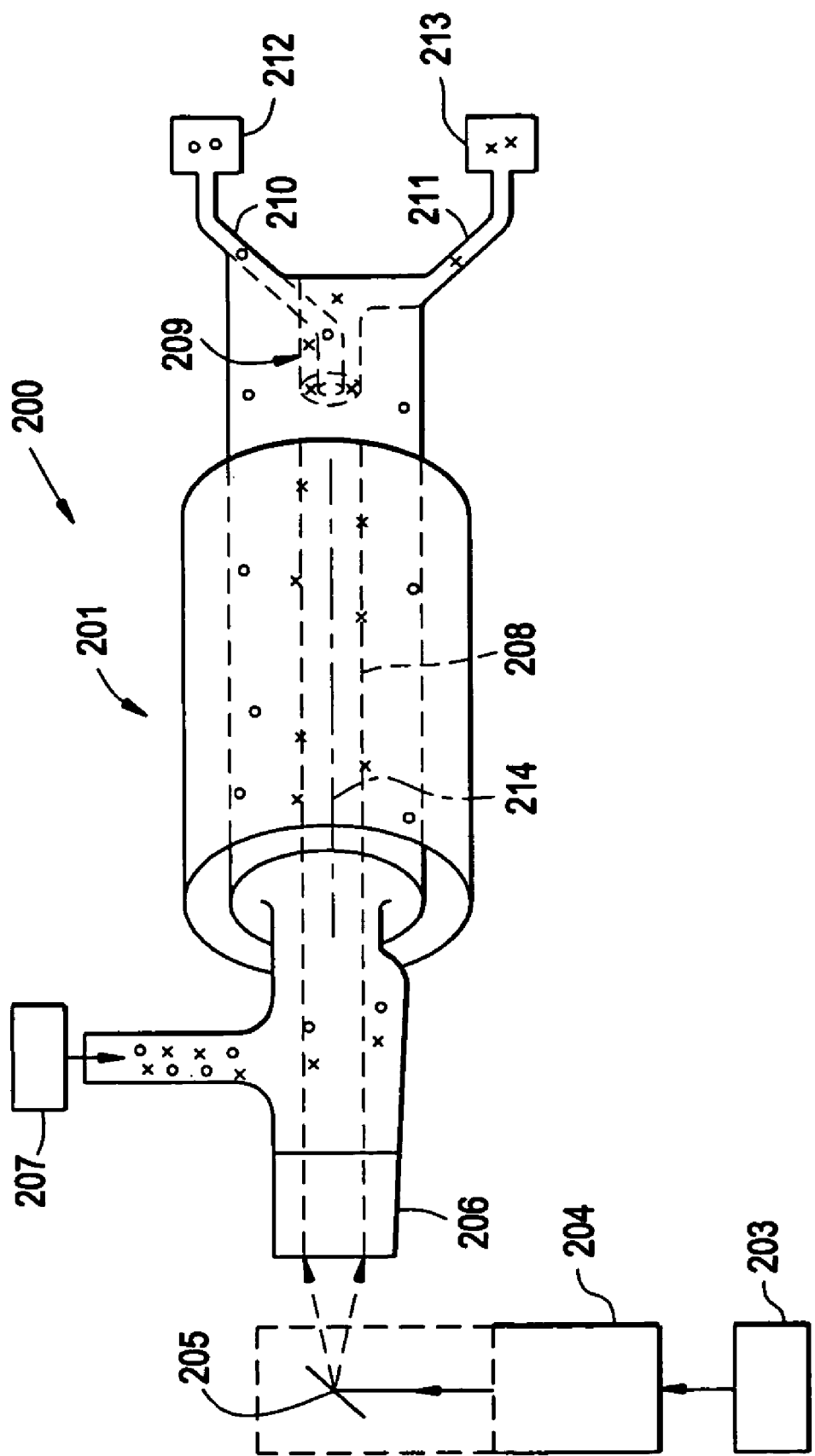
FIG. 2 is a perspective schematic diagram showing another embodiment of a doughnut-shaped eigenmode used in a liquid core waveguide apparatus for sorting particles, consistent with the present invention.

FIG. 2 shows another embodiment consistent with the present invention, including a doughnut-shaped eigenmode (i.e., a Bessel function) in a cylindrically shaped waveguide or flow tube 201, the high intensity cross-sectional pattern which forms a doughnut shape. A light source 203 (i.e., laser) provides a light beam, and along with coupling optics 204, including an SLM 205, for example, emits light into the waveguide 201 via a light input area 206.

If the eigenmode is a Bessel function, the light input would be a Bessel beam, which is a light intensity pattern which can be described by an nth-order Bessel function as referenced in D. McGloin and K. Dholakia, Contemporary Physics, Vol. 46, No. 1, January-February 2005, 15-28. A special property of this pattern is that there is no change in the cross-section as the beam propagates, ideally, and thus the beam can be considered diffraction free or propagation invariant. This means that Bessel beams may form a diffraction limited spot that is extended along the optical axis 214 which could be defined relative to a liquid core waveguide axis.

In FIG. 2, a solution with particles/cells for sorting, is input from a reservoir 207 (i.e., pumped into the waveguide 201), and particles that have a higher refractive index will be preferentially attracted to the tube of light or doughnut region 208 (i.e., the "x" particles), while the particles with relatively lower indices of refraction will stay in the central region (i.e., the "o" particles). The particles are collected via an annular-shaped collection output 209, downstream of the waveguide 201. The particles which were attracted to the doughnut-shaped region 208 are collected via collection port 211 and the remainder of the particles (i.e., the "o" particles), are collected via collection portion 210, which collects particles that were repelled by the doughnut-shaped region 209, or which have a lower refractive index in the central region. The particles are collected into fractions 212, and 213. Accordingly, the device 200 can effectively optically sort the particles/cells inputted into the device 200.

In another embodiment consistent with the present invention, FIG. 3A shows an apparatus 300 for sorting particles/cells, including a liquid core waveguide 301, into which light is introduced from a light source 302 (i.e., laser), and via coupling optics 303, and a spatial light modulator (SLM) 304. The SLM 304 introduces multiple eigenmodes or a time varying series of eigenmodes into the liquid core waveguide 301, which creates a controlled time dependent variation in the cross-sectional intensity profile for use in sorting.

Thus, by selectively launching in a few of the liquid core waveguide's 301 eigenmodes, and using the coupling between these eigenmodes and their distinctive propagation characteristics, a controlled time dependent variation in the cross-sectional intensity profile can be achieved. In addition, the eigenmode or light pattern that is launched into the liquid core waveguide 301 may be modulated between several or many patterns resulting in an actively applied dynamic light distribution pattern. These dynamic patterns (both passive mode-coupling and/or active mode modulation) which may include patterns created by more than one laser source 302 at different wavelengths, may be designed to optimally sort the particles at hand.

For example, a cross-sectional view along line B shows a light pattern with a doughnut mode and a central Bessel spot in FIG. 3B, where the "x" particles are attracted to the outer tube of light, whereas, further downstream, along line C, the cross-sectional view shown in FIG. 3C shows the light energy in just a doughnut mode. However, by using the SLM 304, these cross-sectional "custom light intensity patterns" can be varied in time or space (or both).

(The solution with particles is not shown in FIGS. 3A-C for simplicity, but the particles sorted would be sorted using designs similar to that mentioned above, and as with the other embodiments, the sorted particles would be collected via a collection structure 306).

Figure 4A:
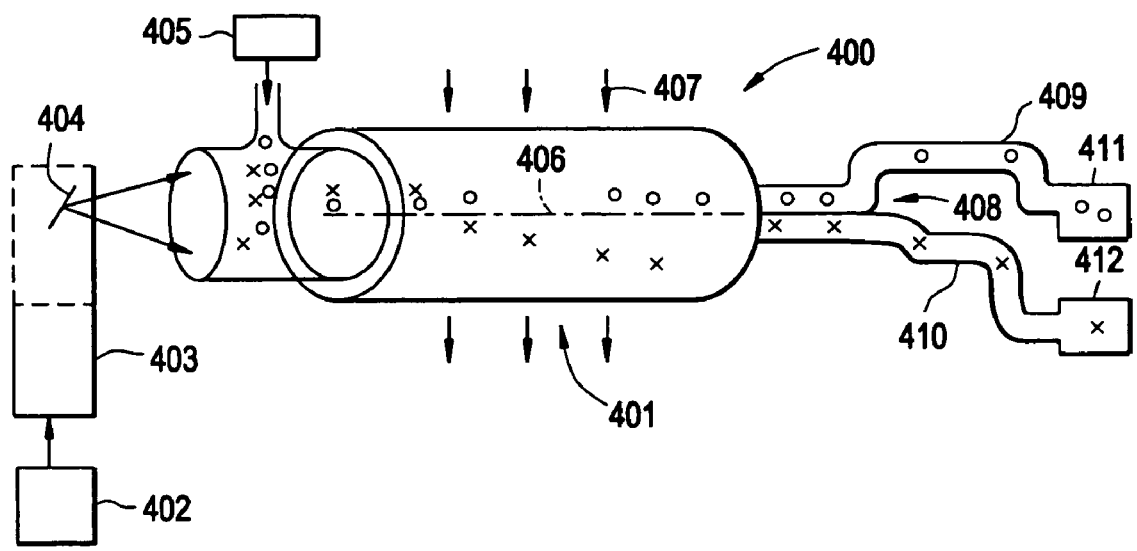
FIG. 4A is a perspective schematic diagram showing yet another embodiment of a liquid core waveguide apparatus for sorting particles, consistent with the present invention, where hydrodynamic forces controlled by the fluid input and gravitational forces, are combined with optical forces within the waveguide to selectively direct the desired particles into outlet collection regions for sorting.

FIG. 4A shows another embodiment of an apparatus 400 for sorting particles/cells, including a liquid core waveguide 401, into which light is introduced via a light source 402 (i.e., laser), coupling optics 403, and a spatial light modulator (SLM) 404.

FIG. 4A shows how eigenmodes can selectively be launched into the fiber 401 using a computer generated hologram generated via the SLM 404, which is then spatially filtered and focused into the tubing 401.

Hydrodynamic forces controlled by the fluid input 405, through which the solution containing the particles/cells to be sorted is introduced from a reservoir 405, and gravitational forces 407 are combined with optical forces within the waveguide 401, to selectively direct the desired particles into an outlet collection area 408, for sorting. Particles attracted to the light, which are shown as flowing along the optical axis 406 of the waveguide 401, end up in the top output channel 409 and into collection reservoir 411, since they do not settle as quickly and move to the bottom of the waveguide 401, as do the "x" particles, which are repelled by the light and are acted upon by gravitational forces to end up in collection reservoir 412 via bottom output channel 410.

Figure 4B:
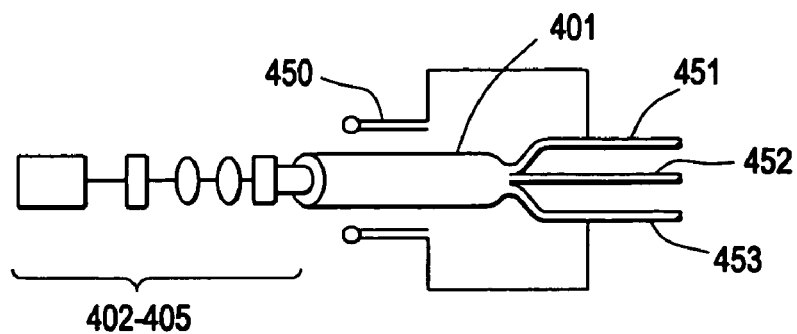
FIG. 4B is an alternative embodiment of FIG. 4A, where electric or magnetic fields can be used in combination with optical forces within the waveguide to assist in sorting particles into different output channels.

In an alternative embodiment, FIG. 4B shows how electric or magnetic fields applied using electrodes 450 can be used in combination with optical forces within the waveguide to assist in sorting particles into different output channels 451-453.

Figure 5:
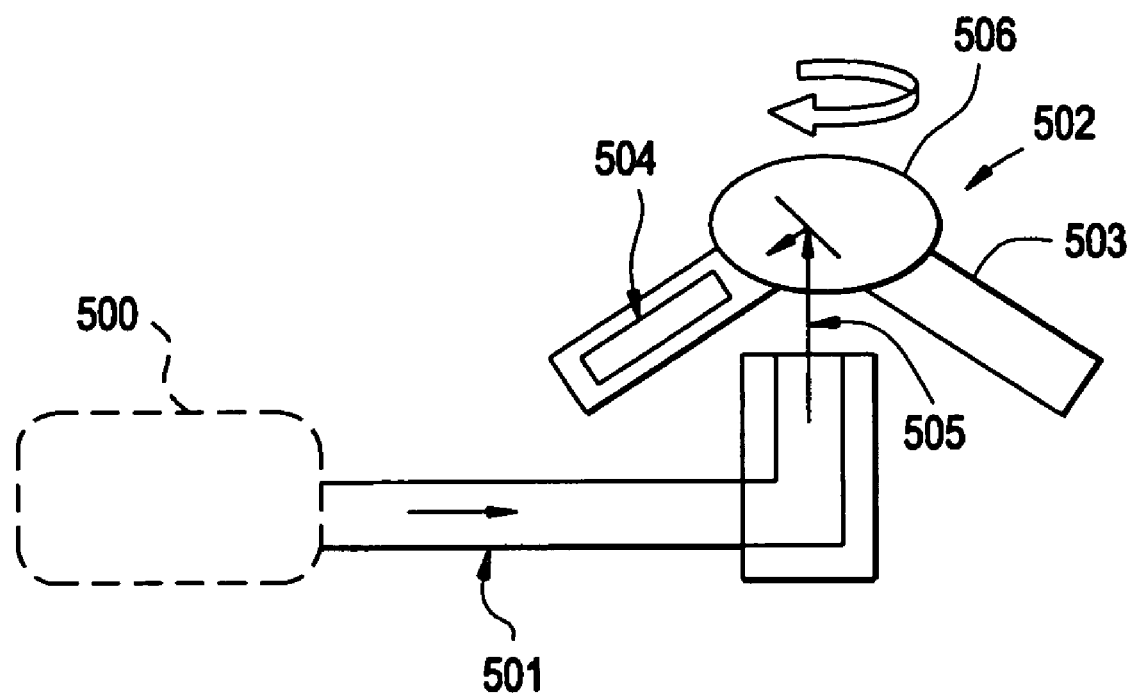
FIG. 5 is a schematic diagram of yet another embodiment of an apparatus for sorting particles/cells, consistent with the present invention, wherein the apparatus is integrated into a centrifuge.

In yet another alternative embodiment, FIG. 5 illustrates how the light from a light source and coupling optics, including a spatial light modulator 500, such as those described above in FIG. 1, is directed into the waveguide 501, and integrated into a centrifuge 502 with the liquid-core waveguide 501 containing a density gradient chamber 504 for the purposes of sorting on the basis of optical characteristics as well as density.

In other words, the liquid solution flowed into the tubing 501 may also form a density gradient, and a device 500 that fits into a centrifuge 502 would provide an additional physical parameter to separate the nanoparticle fractions in solution (i.e., fractionation as a result of differential responses to light fields in combination with density). In this embodiment, optical coupling into the rotor 503 of the centrifuge 502, can occur through the axis of the rotor 503. (Note there is an air gap 505 between the rotor 503 and the spindle 506).

Figure 6A:
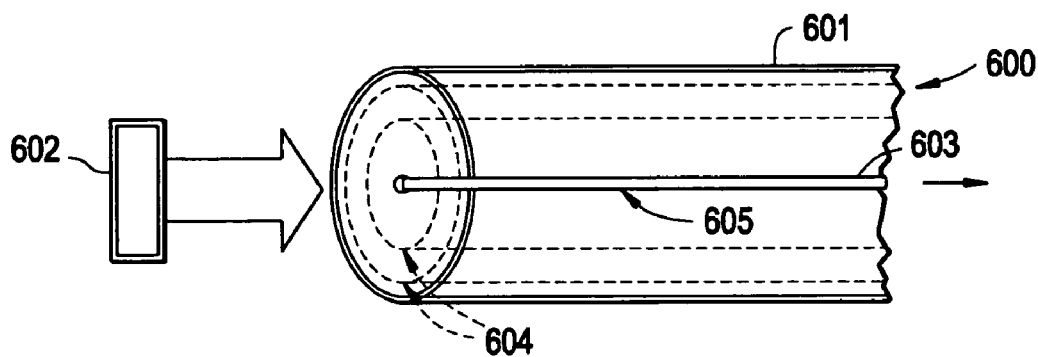
FIG. 6A is a schematic diagram of a liquid core waveguide showing a Bessel beam eigenmode which is launched therein, according to yet another embodiment consistent with the present invention.

In yet another embodiment consistent with the present invention, one specific eigenmode or "custom light intensity pattern" for sorting which uses Bessel beams, is disclosed in the apparatus 600 shown in FIG. 6A. This embodiment involves specifically introducing Bessel Beams into the liquid core waveguide 601 (which would be an example of one type of eigenmode).

FIG. 6A shows a Bessel beam light intensity pattern within a liquid core waveguide 600 showing propagation along the optical axis 603 and the central high intensity light line 605 which may act as a line trap, trapping microscopic objects. Thus, objects (i.e., particles, cells, nanoparticles, etc.) flowing within the liquid core waveguide medium exposed to the Bessel beam intensity pattern or line of high intensity light can be trapped by optical forces and be confined along the line 605 defined by the optical axis 603 (the other arrows 604 show the rings of local maximum and minimum). The optical (photon) pressure directed down the optical axis 603 along this central core spot may also propel objects downstream, along the central core/line trap 605.

Figure 6B:
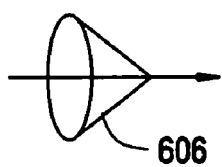
FIG. 6B is a schematic diagram of an axicon used with the embodiment of FIG. 6A.
Figure 6C:
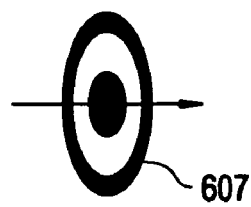
FIG. 6C is a schematic diagram of an annular aperture used with the embodiment of FIG. 6A.
Figure 6D:
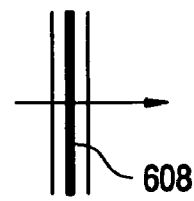
FIG. 6D is a schematic diagram of an annular aperture used with the embodiment of FIG. 6A.

It is known that Bessel beams may be formed by shining light through an axicon optical element (conical shaped lens) 606 (see FIG. 6B) or through an annular aperture 607 (see FIG. 6C) in the back focal plane of an imaging lens which allows only a restricted set of k-vectors through it. Alternatively, Bessel beams may also be formed by shaping light "holographically" i.e., using a diffractive optical element 608 (see FIG. 6D) to create the axicon hologram which is relayed to the back aperture plane of an imaging lens (i.e., objective) as shown in FIG. 6A.

FIG. 6A, as described above, and with reference to the embodiment of FIG. 1, includes coupling optics (including 602) which can launch eigenmodes into the fiber using a computer generated hologram which is then spatially filtered and focused into the tubing 601. Thus, as stated above, a central spot blocker for the k=0 component at the common focal plane, blocks out the $0^{th}$ order beam off the surface of the spatial light modulator, and allows the cells with the higher Q factor to be guided by the evolving mode profile, while the lower Q factor cells will be significantly less optically entrained, allowing the cells to be fractionated depending on their cross-sectional position.

Figure 7:
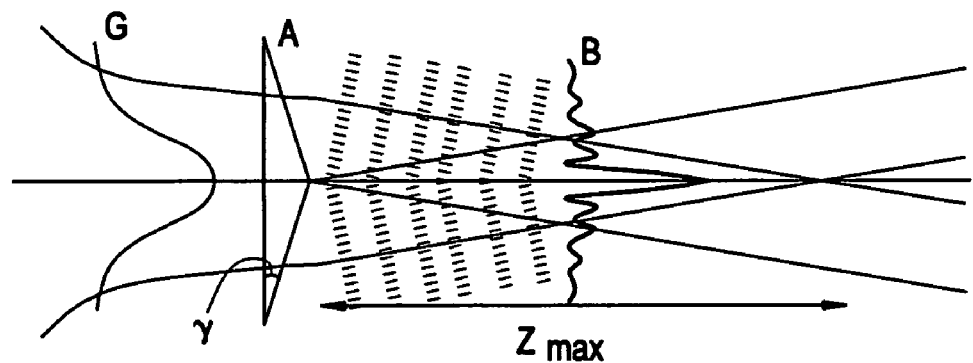
FIG. 7 is a prior art schematic diagram of a Bessel beam interaction.

FIG. 7 is taken from D. McGloin and K. Dholakia, Contemporary Physics, vol. 46, No. 1, January-February 2005, 15-28, and A represents the axicon, and γ is the opening angle of the axicon. $Z_{max}$ is the propagation distance of the Bessel beam. B illustrates the formed Bessel beam with the maximum at the central line, with local maxima defining the rings away from the axis. G represents the input beam with a Gaussian input profile.

Practically, the length the optical spot propagates along the optical axis, $Z_{max}$, is governed by the radius of the imaging lens, or by the width of the Gaussian beam ($w_0$) illuminating the imaging lens as defined in FIG. 7, where n is index of refraction of the axicon material and γ is the opening angle of the axicon.

$$Z_{max} \approx w_0/\theta \text{ where } \theta=(n-1)\gamma$$

However, in the present invention, Bessel beams are used as a method to sort/propel particles/cells within a liquid-core waveguide, by extending the Bessel beam's line length arbitrarily inside the waveguide.

One alternative embodiment of the present invention could use a static solution suspension where the light would act as a source of particle propagation creating a flow field through the center of the wavelength 601. For example, in FIG. 1, the pump 113 would be replaced with just a reservoir that allows diffusion limited entry of particles into the fluid input 114.

While it has been shown that Bessel beams may reform after being partially obstructed along the optical axis, an alternative method of regeneration of the beam as disclosed by the present invention, is to launch it within a reflective/totally internally reflective hollow-core cylinder (liquid core waveguide).

Figure 8:
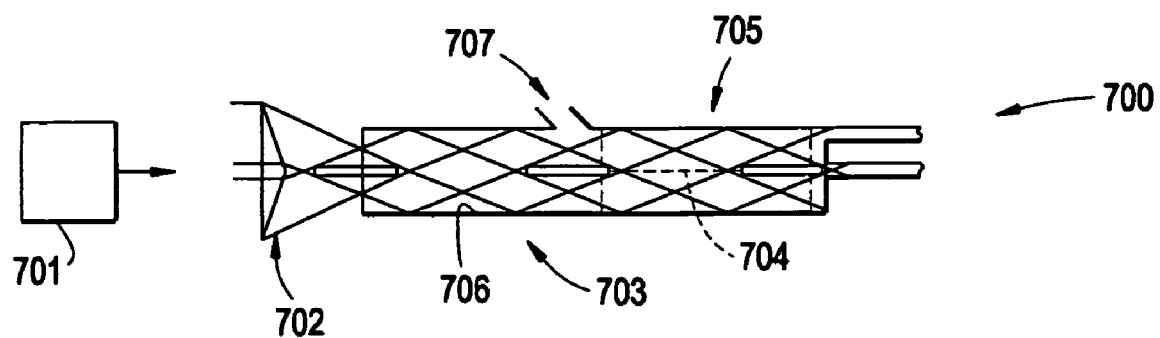
FIG. 8 is a schematic diagram of yet another embodiment of a waveguide used in an apparatus for sorting particles/cells consistent with the present invention, showing a repeating Bessel beam.

In one example of this embodiment consistent with the present invention, FIG. 8 shows an apparatus 700 including this repeating Bessel beam embodiment, which includes a laser 701, axicon 702, and hollow cylinder 703 with a highly reflective, sub-wavelength roughness inner surface. The reflective inner surface of the cylinder or waveguide 703 allows the rays, after they have converged to make the Bessel beam, to be reflected back towards the optical axis 704 so that another Bessel beam may be reformed (see repeating section 705). The interval of the Bessel beams being reformed may be tuned by modifying appropriate parameters such as the radius of the beam-guide.

The parallelism and flatness of the inner surface of this cylinder 703 must be sufficiently high for this method to be practical. A mirror-like finish may be applied to the inner surface 706, or the inner surface 706 may be coated with a material that permits total internal reflection (for the given wavelength and refractive index of the solution, as described above with respect to FIG. 1).

For the purposes of sorting particles using trapping/propulsion, such a cylinder 703 is filled with a liquid (solution) containing some dilution of particles, inputted via flow input 707. As mentioned in the above earlier embodiments using eigenmodes, such a device 700 may be used for particle/cell sorting on the basis of the different Q values for each fraction of particles/cells. As stated above, Q is the proportionality constant between the light intensity impinging on the particle and the resulting force imparted. Particle types (or cells) with higher Qs are more readily pushed by the force arising from photon pressure.

Thus, in this embodiment in FIG. 8, by repeatedly creating diffraction-limited light patterns suitable for optical trapping, one can reuse un-scattered laser light that would otherwise be lost using normal Gaussian optical traps. By reducing laser power and simplifying the sorting device to a few components that can be produced inexpensively and in large numbers. This offers a cheap and compact apparatus capable of separating different populations of objects based on optical characteristics. If the reflection angles are sufficiently obtuse, a liquid-core fiber optic may be used as an alternative to the cylinder 703.

As stated above with respect to FIG. 6, in an alternative embodiment, the present invention could be applied to a static solution suspension where the light acts as a source of particle propagation, or alternatively, a solution may be actively pumped through the center of the waveguide 703, creating a flow field. FIG. 1 illustrates the pump and reservoir to achieve this result.

Further, as stated above and shown in the Figures, gravity, magnetic, and/or electric fields may be used as additional means to sort particles/cells in combination with the differential action of optical/hydrodynamic fields, in the Bessel beam waveguide. Magnetic and/or electric fields may be introduced through the surfaces of the waveguide, allowing additional fractionation capabilities based on differential particle interactions with these fields. Gravity, acting vertically, may also be used to differentiate fractions based on density.

In yet another embodiment consistent with the present invention, the apparatus takes advantage of liquid core waveguides for specifically sorting nanoparticles and involves the introduction of sub-wavelength pores within the waveguide. One important feature of this embodiment of the present invention is the presence of sub-wavelength input and output ports in the waveguide (for example, see FIG. 1) which allows nanoparticles to flow into it, and which allows subsequent interactions with the high intensity light fields. The openings in the waveguide that are sub-wavelength in the length scale would not result in significant light loses, yet would still allow the introduction of nanoparticles into the structure. While limited to sorting very small particles (relative to the wavelength of light) this embodiment does not require particles to be flowed through the length of the waveguide meaning the output collection region does not have to be at the end of the waveguide.

Figure 9A:
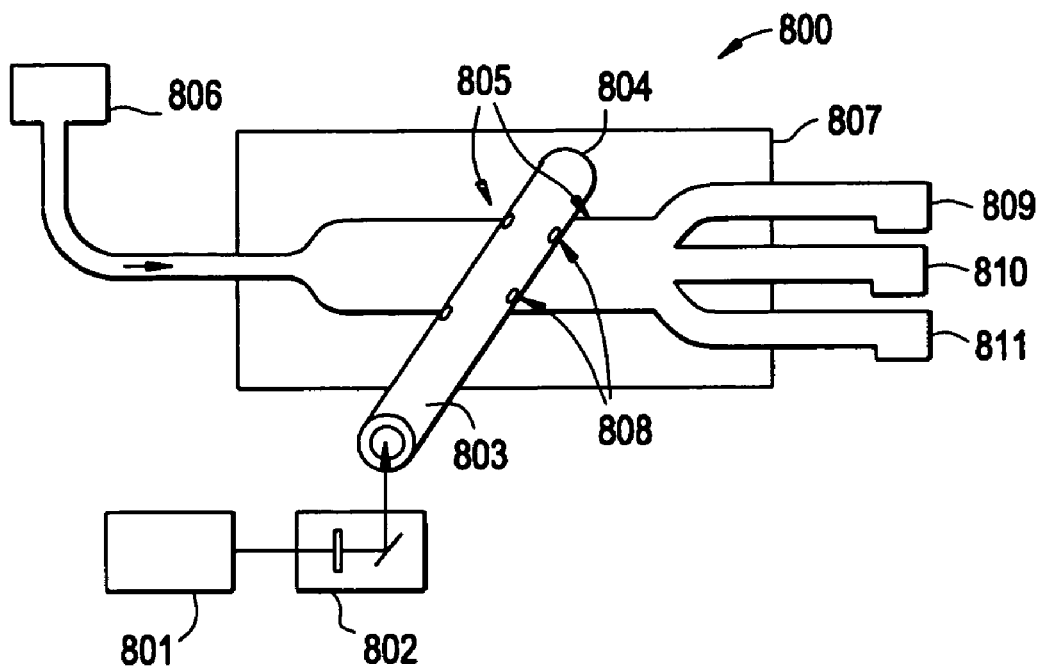
FIG. 9A is a schematic diagram of yet another embodiment of a liquid core waveguide of an apparatus for sorting particles/cells consistent with the present invention, including nanoporous openings on the sides and incorporated on a flow chip.
Figure 9B:
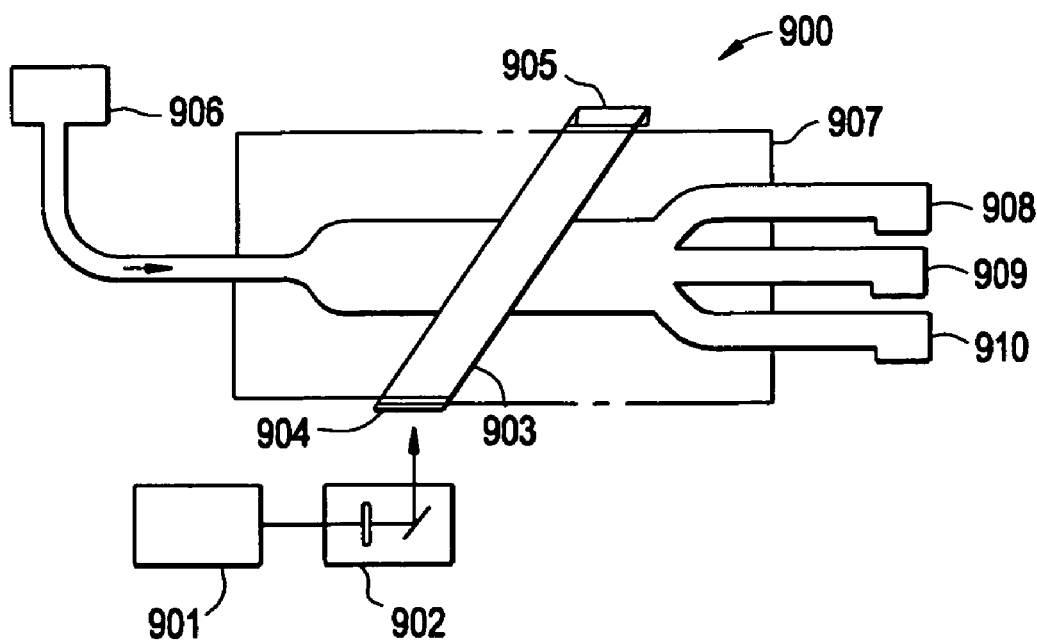
FIG. 9B is a schematic diagram of an alternative embodiment to FIG. 9A, including a resonant cavity with nanoporous sides incorporated onto a similar flow chip.

In one exemplary embodiment of an apparatus 800 for sorting particles/cells, consistent with the present invention, light can be confined within a liquid-core waveguide (see FIG. 9A) or a resonant cavity (see FIG. 9B).

In FIG. 9A, a laser 801 and light coupling optics 802 launch an eigenmode pattern into a liquid core waveguide 803, but the end 804 of the waveguide 803 is capped and the liquid flow is moving across through the sides 805 of the waveguide 804. The fluid is pumped from a reservoir 806 but a flow chip 807 can be used to direct the solution around the waveguide 803 passing through the nanoporous input holes 808 on the sides 805. Nanoparticles suspended within the fluid interact with the custom light pattern inside the waveguide 803 and have their position deflected so that when the flow carries the particles out of the waveguide 803 on the other side, the nanoparticles can be easily sorted into different output channels 809, 810, 811.

The exemplary embodiment in FIG. 9B shows a similar sorting apparatus 900, with laser 901, and coupling optics 902, generating light, with the apparatus 900 being created using a resonant cavity 903 with nanoporous sides instead of a waveguide (as shown in FIG. 9A). A flow chip 907 similar to that of FIG. 9A is used to introduce nanoparticles and direct flows across the light field in the cavity 903 and on towards output channels 908-910 for collection. A resonant cavity 903 typically has one partially reflective end mirror 904 through which light is initially launched into the system from a laser 901, and the other end mirror 905 can be totally reflective. (Note, using diffractive elements in the coupling optics 902 to generate "custom light intensity patterns" or eigenmodes may still be used as discussed previously).

The liquid used in the present invention can be any disperse suspension of nanoparticles (particles with diameters less than 200 nm), which are to be sorted by their physical and optical properties based on their reaction to the different net forces in a light field (i.e., Q value).

An array of sub-wavelength sized holes could be arranged through any surface of the liquid-core waveguide/resonant cavity 903. Such a nanoporous surface would significantly increase the throughput of nanoparticles through the waveguide 903, increasing the rate of sorting. The pore density on such a surface would have to be sufficiently low to prevent appreciable light losses.

Figure 10:
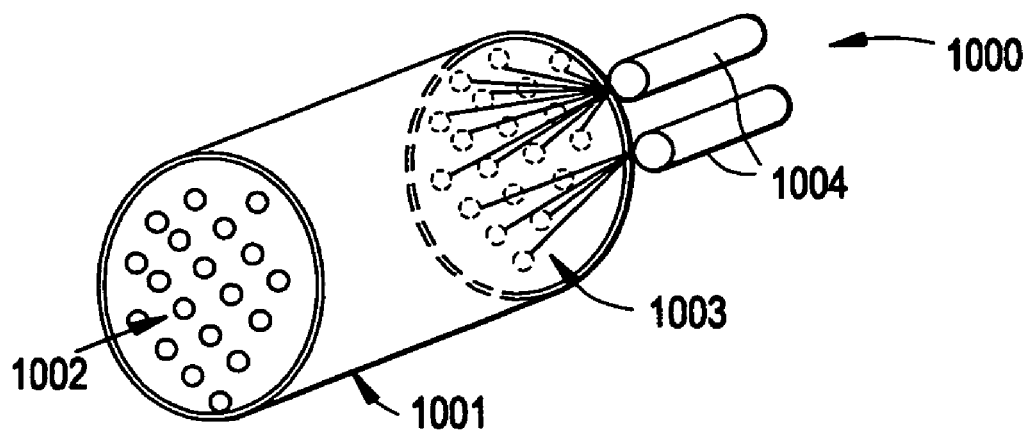
FIG. 10 is a schematic diagram of yet another embodiment of a liquid core waveguide of an apparatus for sorting particles/cells consistent with the present invention, showing a nanoporous membrane as input and output interface.

In another embodiment consistent with the present invention, an apparatus 1000 for sorting particles/cells, would include a structure where the whole stream of solution can be introduced into the liquid-core waveguide 1001 (see the arrow) through the ends using nanoporous membranes, allowing all of the solution to interact with the light fields inside the liquid core waveguide 1001, as shown in FIG. 10.

FIG. 10 shows an optical layout of liquid-core waveguide 1001 (the surrounding structure is not shown, for simplicity), coupled with a nanoporous membrane on the front 1002, and back 1003 of the waveguide 1001, allowing the whole flow to interact with the light field inside the waveguide 1001. Fractions may be collected at the end of the flow stream via output channels 1004 as in earlier embodiments.

Note the liquid core waveguide 1001 in this example, has a spatially varying light distribution or "custom light intensity pattern" (as determined by the eigenmodes described above with respect to the other Figures). The equilibrium position of each fraction of nanoparticles in this stream would be a function of the net buoyant, hydrodynamic and optical forces and result in each fraction occupying distinct positions in the flow field. The flow in the optical waveguide/resonant cavity can then be split into separate channels to be able to collect each fraction.

As one of ordinary skill in the art would contemplate, there are other embodiments consistent with the present invention which would use variations of the "sub-wavelength" input and outputs, which allow nanoparticles to be sorted. Further, other combinations of using "resonant cavities" in combination with liquid core waveguides, and a "resonant cavity" in combination with "custom light intensity patterns" for sorting, as described above with respect to FIG. 1 and others, are relevant to all embodiments of this invention.

Note since only small "sub wavelength" openings are being used, only small objects can be sorted, but this means the liquid core waveguide to be used can also be smaller, like a single mode optical fiber with a hollow core, as opposed to the larger examples which can be used with the blood sorting applications, for example.

Further, "nanoparticle" can refer to inorganic particles (like quantum dots), biological objects (such as viruses, DNA, suspended vesicles, etc.), or other organic/inorganic materials (like modified particles or polymer suspensions), as long as the size scale of the objects to be sorted is "sub-wavelength" and can be introduced through sub-wavelength inputs to be exposed to optical forces within the waveguide without allowing substantial light loss.

Specifically, additional embodiments of the present invention are described as follows:

As mentioned above, and shown earlier in FIGS. 4A and 5, gravity, magnetic, and/or electric fields may also be used as additional means to sort nanoparticles in combination with the differential action of optical/hydrodynamic fields, within this invention.

Figure 11:
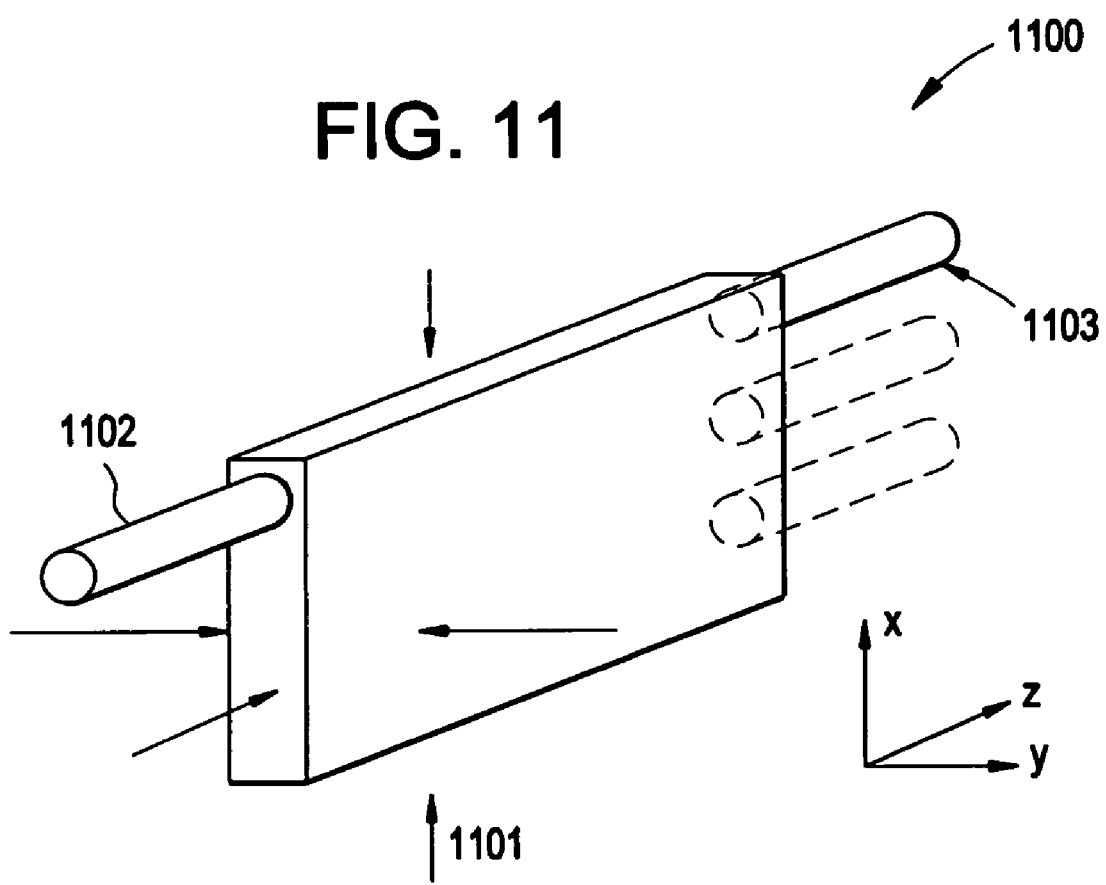
FIG. 11 is a schematic diagram of yet another embodiment of a liquid core waveguide of an apparatus for sorting particles/cells consistent with the present invention, showing a square instead of cylindrical waveguide structure, with sub-wavelength fluid inputs and outputs.

In yet another embodiment consistent with the present invention, an apparatus 1100 for sorting particles/cells involves using a liquid core waveguide 1100 which is also a resonant cavity, coupled with a nanoparticle flow channel allowing the whole flow to interact with the light field inside the waveguide 1101 (see FIG. 11). Again the whole stream can be introduced into the liquid-core waveguide 1101 (see arrow) through sub-wavelength inputs 1102. Additional light fields 1101 formed by creating resonant cavities in the x and or y directions may also be formed to tune the light field distribution. The flow in the optical waveguide/resonant cavity 1101 can then be split into separate channels 1103 to be able to collect each sorted fraction.

In addition to the "custom light pattern" established within the liquid core waveguide 1100 which has a light field distribution in x, y, and z, set up by launching in laser or non-laser light through a suitable window(s) (i.e., introducing eigenmodes as described earlier), in other embodiments consistent with the present invention, resonant cavities along y and x may also be set up with suitably reflective inner surfaces, and light sources.

Figure 12A:
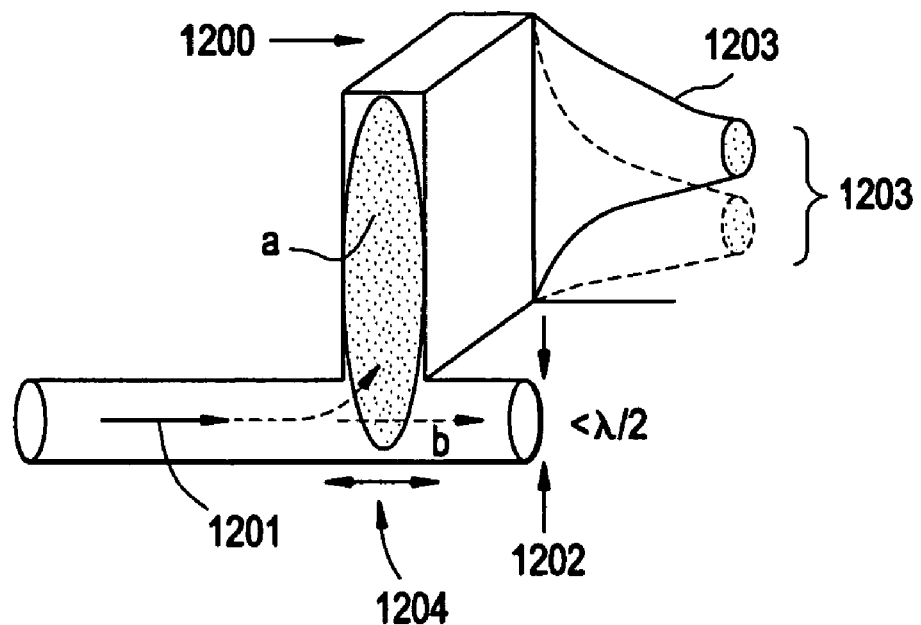
FIG. 12A is a schematic diagram of yet another embodiment of a liquid core waveguide of an apparatus for sorting particles/cells consistent with the present invention, showing only a portion of the flow introduced through a sub-wavelength opening (nanochannel) into the liquid core waveguide.

In addition, in another embodiment consistent with the present invention, liquid core waveguides 100, 1200 may have non-cylindrical symmetry (i.e., rectangular, for example) as shown in FIGS. 11 and 12A, B.

In yet another embodiment consistent with the present invention, only a portion of the flow is introduced or exposed to light from the liquid core waveguide 1200 (see FIG. 12A) through a sub-wavelength opening 1201 (surrounding structure as in previous embodiments, is not shown, for simplicity).

In one example, FIG. 12A shows an optical layout of liquid-core waveguide 1200 coupled with a nanoparticle flow channel 1201. The sub-wavelength opening 1202 in the liquid-core waveguide 1200 keeps the light from propagating out of the cavity. Flow a is optically forced into the waveguide 1200, flow b is the through flow stream. FIG. 12A shows how a nanoparticle flow can be exposed to a portion of the "custom light intensity pattern" from the liquid core waveguide 1200, and depending on the nanoparticles interaction with the light field inside, and results in either:

1) Diversion into the waveguide flow with or without further fractionation (arrow a, FIG. 12A), or 2) Continuation of the flow containing fraction(s) that did not interact significantly (arrow b, FIG. 12A).

The nanoparticle flow that is attracted into the waveguide 1200 will interact with the light field down the length of the chamber/cavity (1204 being the interaction distance).

Figure 12B:
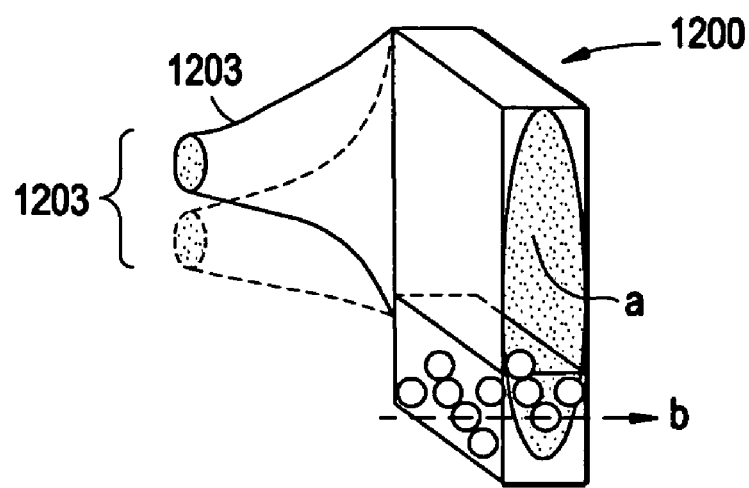
FIG. 12B is a schematic diagram of yet another embodiment of a liquid core waveguide of an apparatus for sorting particles/cells consistent with the present invention, showing a nanoporous membrane instead of a nanochannel.

In another embodiment, FIG. 12B is similar to FIG. 12A, but shows the nanoporous surfaces for flowing nanoparticle solution into the liquid-core waveguide 1200, and flowing non-interacting nanoparticle solution (flow stream b) out of this structure, as well as nanoparticle fractions that have been optically guided into the liquid-core waveguide and further sorted at output 1203.

In other embodiments consistent with the present invention, and as discussed above, the light field may also be an evolving set of eigenmodes which may be introduced with a computer controlled spatial light modulator (see above with respect to FIG. 1, for example), allowing sorting based on differential optical entrainment. At the end of the chamber/cavity, based on the final equilibrium positions in the flow stream, the flow may be sorted into separate fractions.

Finally, in other embodiments consistent with the present invention, and as described above, the liquid solution flowed into the waveguide may be purified by sorting out particles which interact with the light and collecting the remaining solution instead of the particles.

It should be emphasized that the above-described embodiments of the invention are merely possible examples of implementations set forth for a clear understanding of the principles of the invention. Variations and modifications may be made to the above-described embodiments of the invention without departing from the spirit and principles of the inven-

What is claimed is:

1. An apparatus for sorting particles comprising:
   a light source which emits a light beam;
   a flow structure through which said solution flows; and
   a diffractive optical element;
   wherein said diffractive optical element modulates said light beam and generates a custom light intensity pattern in said flow structure; and
   wherein said solution contains particles and said particles are optically entrained and fractionated depending on a cross-sectional position of said particles in said flow structure.

2. The apparatus according to claim 1, wherein said solution is blood.

3. The apparatus according to claim 2, wherein an internal diameter of said flow structure is relatively larger than a wavelength of light in said flow structure in order to efficiently flow said solution through said flow structure.

4. The apparatus according to claim 1, wherein said flow structure is a doughnut-shaped eigenmode.

5. The apparatus according to claim 4, wherein said eigenmode is a Bessel function.

6. The apparatus according to claim 5, wherein a Bessel beam light intensity pattern is propagated through said flow structure; and
   wherein optical pressure directed down an optical axis of a central core of said flow structure, propels objects in said solution downstream along said central core.

7. The apparatus according to claim 5, further comprising:
   an imaging lens; and
   an axicon optical element through which said light beam is shone in a back focal plane of said imaging lens, to form said Bessel beam.

8. The apparatus according to claim 5, further comprising:
   an imaging lens; and
   an annular aperture disposed in a back focal plane of said imaging lens, through which said light beam is shone to form said Bessel beam.

9. The apparatus according to claim 5, further comprising:
   an imaging lens;
   wherein said light beam is shaped holographically by said diffractive optical element, to create an axicon hologram, which is relayed to a back aperture of said imaging lens, to form said Bessel beam.

10. The apparatus according to claim 4, wherein the Bessel beam forms a diffraction limited spot extended along an optical axis of said flow structure.

11. The apparatus according to claim 10,
    wherein particles in said solution which have a relatively higher refractive index are preferentially attracted to a doughnut region of said flow structure, and said particles with a relatively lower refractive index will remain in a central region of said flow structure.

12. The apparatus according to claim 11, further comprising:
    a collection output disposed downstream of said flow structure, which collects said particles in a plurality of collection portions.

13. The apparatus according to claim 12, wherein said collection output includes at least a top output channel and a bottom output channel, and gravitation forces act upon particles in said solution to move said particles into said bottom output channel.

14. The apparatus according to claim 12, further comprising:
    a plurality of electrodes, wherein one of electric and magnetic fields applied by said electrodes act upon said flow structure to move particles in said solution into said collection portions.

15. The apparatus according to claim 12, further comprising:
    means for forming a density gradient within said flow structure, such that fractionation of particles in said solution results from differential responses to light fields in combination with density.

16. The apparatus according to claim 12, wherein said density gradient means fits into a centrifuge.

17. The apparatus according to claim 4, wherein said diffractive optical element is a spatial light modulator, and said spatial light modulator introduces at least one of a plurality of eigenmodes and a time varying series of eigenmodes into said flow structure, which creates a controlled time-dependent variation in a cross-sectional intensity profile of said flow structure.

18. The apparatus according to claim 17, wherein said eigenmode that is introduced into said flow structure is modulated into a plurality of light intensity patterns resulting in an actively applied dynamic light distribution pattern.

19. The apparatus according to claim 18, wherein said light intensity patterns can be varied in at least one of time and space.

20. The apparatus according to claim 1, wherein said diffractive optical element is an axicon optical element.

21. The apparatus according to claim 20, wherein said flow structure has one of a partially and a totally reflective inner surface, and a sub-wavelength roughness interior surface.

22. The apparatus according to claim 21, wherein said flow structure is a cylinder, and said cylinder includes a reflective inner surface which allows said light beam to form and reform Bessel beams.

23. The apparatus according to claim 22, wherein said reflective inner surface is provided by one of a mirror-finish on an inner surface of said cylinder, and a coating disposed on an inner surface of said cylinder.

24. The apparatus according to claim 23, wherein said coating has an index of refraction which is less than that of an index of refraction of said solution flowing through the flow structure.

25. The apparatus according to claim 22, wherein sorting of particles in said solution is accomplished based on Q values of said particles.

26. The apparatus according to claim 22, wherein an interval of the Bessel beams being reformed may be tuned by modifying a radius of said light beam.

27. The apparatus according to claim 20, wherein said flow structure is a hollow core fiber optic.

28. The apparatus according to claim 1, wherein said particles are nanoparticles.

29. The apparatus according to claim 28, further comprising:
    a flow chip into which said solution with said particles is introduced, said flow chip having a plurality of output channels;
    wherein said flow structure is a waveguide including input holes in sides of said waveguide, said waveguide being disposed across said flow chip such that said solution from said flow chip flows through said waveguide.

30. The apparatus according to claim 28, wherein nanoparticles in said solution interact with said custom light pattern within said waveguide, and have their positions deflected, such that said particles flow out of said waveguide and are sorted into different of said output channels.

31. The apparatus according to claim 29, further comprising:
a plurality of electrodes, wherein one of electric and magnetic fields applied by said electrodes act upon said flow structure to sort said nanoparticles.

32. The apparatus according to claim 28, further comprising:
a flow chip into which said solution with said particles is introduced, said flow chip having a plurality of output channels;
wherein said flow structure is a resonant cavity disposed across said flow chip such that said solution from said flow chip is sorted as it flows through said resonant cavity.

33. The apparatus according to claim 32, wherein said resonant cavity includes a partially reflective end mirror at one end, and a reflective mirror at another end.

34. The apparatus according to claim 33, wherein said resonant cavity includes a plurality of sub-wavelength sized holes on its surface through which said nanoparticles are sorted.

35. The apparatus according to claim 1, wherein said solution is introduced into said flow structure via nanoporous membranes at ends of said flow structure.

36. The apparatus according to claim 32, further comprising:
a plurality of electrodes, wherein one of electric and magnetic fields applied by said electrodes act upon said flow structure to sort said nanoparticles.

37. The apparatus according to claim 32, wherein said flow chip includes sub-wavelength inputs.

38. The apparatus according to claim 37, wherein additional light fields are created in x and/or y directions in said resonant cavity, to tune a light field distribution in said resonant cavity.

39. The apparatus according to claim 32, wherein said resonant cavity includes reflective inner surfaces.

40. The apparatus according to claim 27, wherein said flow structure is a single mode optical fiber.

41. The apparatus according to claim 28, wherein said nanoparticles comprise at least one of organic particles, biological particles, and inorganic particles.

42. The apparatus according to claim 28, wherein said nanoparticles are exposed to said custom light intensity pattern within said flow structure, resulting in one of a diversion of a flow of said solution without fractionation, and continuation and outputting of said flow containing fractions that do no interact with one another.

43. The apparatus according to claim 28, wherein said diffractive optical element is a computer-controlled spatial light modulator for producing a spatially varying light distribution from said light beam, and sorting said nanoparticles based on differential optical entrainment.

44. The apparatus according to claim 1, wherein said flow structure comprises a non-cylindrical symmetry.

45. The apparatus according to claim 1, wherein only a portion of said solution is inputted through said flow structure.

46. An apparatus for sorting particles comprising:
a light source which emits a light beam;
a flow structure through which solution flows; and
a diffractive optical element;
wherein said diffractive optical element modulates said light beam and generates a custom light intensity pattern in said flow structure; and
a coating disposed on an inner surface of said flow structure, said coating which has an index of refraction which is less than that of an index of refraction of the solution flowing through the flow structure.

47. The apparatus according to claim 46, wherein said coating is a reflective material which enables total internal reflection at the wavelengths used.

48. The apparatus according to claim 46, wherein $n_{ic}(\lambda) < n_{solution}(\lambda)$, where $n_{ic}(\lambda)$ is said index of refraction of said coating, at wavelength $\lambda$, and where $n_{solution}(\lambda)$ is a refractive index of the solution, $n_{solution}(\lambda)$ at said wavelength $\lambda$.

49. The apparatus according to claim 46, wherein said diffractive optical element is a spatial light modulator, and coupling optics direct said light beam onto said spatial light modulator.

50. The apparatus according to claim 46, further comprising:
a pumping mechanism which introduces said solution into said flow structure.

51. The apparatus according to claim 46, further comprising:
a collection area including a plurality of output channels which collect particles in said solution.

52. The apparatus according to claim 51, wherein said output channels are sub-wavelength in size.

53. The apparatus according to claim 46, wherein said coating has an index of refraction 1.29-1.31.

54. The apparatus according to claim 46, wherein said solution is introduced into said flow structure from a reservoir.

55. The apparatus according to claim 46, wherein said solution is blood.

56. An apparatus for sorting particles comprising:
a light source which emits a light beam;
a flow structure through which said solution flows; and
a diffractive optical element;
wherein said diffractive optical element modulates said light beam and generates a custom light intensity pattern in said flow structure; and
wherein an external portion of said flow structure is made of a material with an index of refraction lower than said solution flowing through said flow structure.

57. An apparatus for sorting particles, comprising:
a light source which emits a light beam;
a flow structure through which solution flows; and
a diffractive optical element;
wherein said diffractive optical element modulates said light beam and generates a custom light intensity pattern in said flow structure; and
a central spot blocker which blocks out a $0^{th}$ order beam from a surface of said diffractive optical element.

58. The apparatus according to claim 57 wherein said solution contains particles and said particles are optically entrained and fractionated depending on a cross-sectional position in said flow structure.

59. An apparatus for sorting particles in a solution comprising:
a laser which emits a light beam;
a flow structure through which solution flows, and into which said light beam is directed; and
means for sorting objects in said solution;
wherein said sorting means includes a diffractive optical element which allows said light beam to act differentially on each of the objects, causing a difference in Q factor, to allow the objects with a higher Q factor to be more optically entrained and sorted from objects with a lower Q factor based on their position in the flow structure.

60. An apparatus for sorting particles comprising:
a light source which emits a light beam;
a liquid core waveguide containing a solution having particles suspended therein;
a central hollow portion through which said solution flows;
wherein particles in said solution enter said central hollow portion and interact with predetermined high-intensity light fields from said light beam, said light fields which entrain said particles such that said particles are directed to predetermined target regions within said hollow portion and sorted based on their position in said central hollow portion.

61. An apparatus for sorting particles comprising:
a laser and optical elements necessary for forming and projecting Bessel beam into said waveguide; and
a flow structure having a central core with a central optical axis therein, said flow structure through which solution flows, and into which said Bessel beam light intensity pattern is propagated, said solution containing objects;
wherein optical pressure directed down said optical axis of said central core of said flow structure, propels objects in said solution which are entrained by said Bessel beam light intensity pattern downstream along said central core of said flow structure, such that said objects are sorted from objects which are not entrained thereby.

62. An apparatus for sorting particles comprising:
a light source which emits a light beam;
a flow structure through which solution flows, and into which said modulated light beam is directed; and
means for optically entraining particles within said solution, to allow said particles to be fractionated depending on their cross-sectional position.

63. A method of sorting objects comprising:
directing a light beam from a light source to a diffractive optical element;
directing said light beam from said diffractive optical element into a flow structure;
generating a custom light intensity pattern in said flow structure using said diffractive optical element;
flowing a solution with particles into said flow structure; and
sorting said particles in said flow structure based on action of said custom light intensity pattern with said particles, to direct said particles into different target regions in said flow structure;
optically entraining and fractionating said particles depending on a cross-sectional position of said particles in said flow structure.

64. The method according to claim 63, further comprising:
outputting said particles into different output channels based on said sorting step.

65. The method according to claim 64, wherein said output channels are sub-wavelength in size.

66. The method according to claim 63, further comprising:
forming a Bessel beam in said flow structure by utilizing a doughnut-shaped eigenmode.

67. The method according to claim 66, wherein said Bessel beam forms a diffraction limited spot extended along an optical axis of said flow structure.

68. The method according to claim 66, further comprising:
separating said particles based on attraction of said particles to a doughnut-shaped region in said flow structure;
wherein particles in said solution which have a relatively higher refractive index are preferentially attracted to said doughnut region of said flow structure, and said particles with a relatively lower refractive index will remain in a central region of said flow structure; and
collecting said particles via a collection output downstream from said flow structure.

69. The method according to claim 68, further comprising:
collecting said particles via a bottom output channel due to gravitational forces acting on said particles.

70. The method according to claim 66, further comprising:
applying one of an electric and a magnetic field to said flow structure to sort said particles.

71. The method according to claim 66, wherein said eigenmode that is introduced into said flow structure is modulated into a plurality of light intensity patterns resulting in an actively applied dynamic light distribution pattern.

72. The method according to claim 71, wherein said light intensity patterns can be varied in at least one of time and space.

73. The method according to claim 66, wherein said light beam is shaped holographically by said diffractive optical element, to create an axicon hologram, which is relayed to a back aperture of said imaging lens, to form said Bessel beam.

74. The method according to claim 73, wherein said diffractive optical element is an axicon optical element.

75. The method according to claim 66, further comprising:
forming a Bessel beam within said flow structure; and
reforming said Bessel beam within said flow structure by reflecting said Bessel beam back towards an optical axis of said flow structure; and
turning said Bessel beam by modifying at least a radius of a beam-guide.

76. The method according to claim 66, wherein said flow structure has one of a partially and a totally reflective inner surface, and a sub-wavelength roughness interior surface.

77. The method according to claim 66, wherein said flow structure is a cylinder, and said cylinder includes a reflective inner surface which allows said light beam to form and reform Bessel beams.

78. The method according to claim 66, further comprising:
applying at least one of a mirror-finish and a coating to an inner surface of said flow structure, to provide a reflective inner surface on an inner surface of said cylinder.

79. The method according to claim 78, wherein said coating has an index of refraction which is less than that of an index of refraction of said solution flowing through the flow structure.

80. The method according to claim 63, wherein said solution is blood.

81. The method according to claim 80, wherein an internal diameter of said flow structure is relatively larger than a wavelength of light in said flow structure in order to efficiently flow said solution through said flow structure.

82. The method according to claim 63, wherein said diffractive optical element is a spatial light modulator, and coupling optics direct said light beam onto said spatial light modulator.

83. The method according to claim 63, further comprising:
forming a density gradient within said flow structure, such that fractionation of particles in said solution results from differential responses to light fields in combination with density.

84. The method according to claim 63, wherein said diffractive optical element is a spatial light modulator, and said spatial light modulator introduces at least one of a plurality of eigenmodes and a time varying series of eigenmodes into said flow structure, which creates a controlled time-dependent variation in a cross-sectional intensity profile of said flow structure.

85. The method according to claim 63, wherein optical pressure directed down an optical axis of a central core of said flow structure, propels objects in said solution downstream along said central core.

86. The method according to claim 63, further comprising: sorting said particles in said solution based on Q factors of said particles.

87. The method according to claim 63, wherein said particles are nanoparticles.

88. The method according to claim 87, further comprising: flowing solution into a flow chip;
disposing a waveguide across said flow chip;
wherein said waveguide includes input holes in sides of said waveguide;
wherein said solution from said flow chip flows through said waveguide.

89. The method according to claim 88, wherein said flow chip includes sub-wavelength inputs.

90. The method according to claim 87, wherein nanoparticles in said solution interact with said custom light pattern within said flow structure, and have their positions deflected, such that said particles flow out of said flow structure and are sorted into different of said output channels.

91. The method according to claim 87, wherein said flow structure is a resonant cavity which includes a partially reflective end mirror at one end, and a reflective mirror at another end.

92. The method according to claim 91, wherein said resonant cavity includes a plurality of sub-wavelength sized holes on its surface through which said nanoparticles are sorted.

93. The method according to claim 92, wherein additional light fields are created in x and/or y directions in said resonant cavity, to tune a light field distribution in said resonant cavity.

94. The method according to claim 92, wherein said resonant cavity includes reflective inner surfaces.

95. The method according to claim 87, wherein said nanoparticles comprise at least one of organic particles, biological particles, and inorganic particles.

96. The method according to claim 63, wherein said solution is introduced into said flow structure via nanoporous membranes at ends of said flow structure.

97. The method according to claim 63, wherein said flow structure comprises a non-cylindrical symmetry.

98. The method according to claim 63, wherein only a portion of said solution is inputted through said flow structure.

99. A method of sorting objects comprising:
directing a light beam from a light source to a diffractive optical element;
directing said light beam from said diffractive optical element into a flow structure;
generating a custom light intensity pattern in said flow structure using said diffractive optical element;
flowing a solution with particles into said flow structure; and
sorting said particles in said flow structure based on action of said custom light intensity pattern with said particles, to direct said particles into different target regions in said flow structure;
wherein an external portion of said flow structure is made of a material with an index of refraction lower than said solution flowing through said flow structure.

100. A method of sorting objects comprising:
directing a light beam from a light source to a diffractive optical element;
directing said light beam from said diffractive optical element into a flow structure;
generating a custom light intensity pattern in said flow structure using said diffractive optical element;
flowing a solution with particles into said flow structure; and
sorting said particles in said flow structure based on action of said custom light intensity pattern with said particles, to direct said particles into different target regions in said flow structure;
wherein said flow structure is a hollow core fiber optic.

101. The method according to claim 100, wherein said flow structure is a single mode optical fiber.

* * * * *